United States Patent
Risse et al.

(10) Patent No.: US 10,946,305 B2
(45) Date of Patent: Mar. 16, 2021

(54) METHOD FOR PRODUCING COCRYSTALS BY MEANS OF FLASH EVAPORATION

(71) Applicants: Centre national de la recherche scientifique, Paris (FR); Université de Strasbourg, Strasbourg (FR); ISL—Institut franco-allemand de recherches de Saint-Louis, Saint-Louis (FR)

(72) Inventors: Benedikt Risse, Wittlingen (DE); Denis Spitzer, Oberschaeffolsheim (FR); Florent Pessina, Strasbourg (FR)

(73) Assignees: CENTRE NATIONAL DE LA RECHERCHE SCIENTIFIQUE (C.N.R.S), Paris (FR); UNIVERSITE DE STRASBOURG, Strasbourg (FR); ISL-INSTITUT FRANCO-ALLEMAND DE RECHERCHES DE SAINT-LOUIS, Saint-Louis (FR)

( * ) Notice: Subject to any disclaimer, the term of this patent is extended or adjusted under 35 U.S.C. 154(b) by 0 days.

(21) Appl. No.: 15/323,654

(22) PCT Filed: Jul. 6, 2015

(86) PCT No.: PCT/EP2015/065335
§ 371 (c)(1),
(2) Date: Jan. 3, 2017

(87) PCT Pub. No.: WO2016/001445
PCT Pub. Date: Jan. 7, 2016

(65) Prior Publication Data
US 2017/0157528 A1    Jun. 8, 2017

(30) Foreign Application Priority Data
Jul. 4, 2014   (FR) ...................................... 1456461

(51) Int. Cl.
*B01D 9/00*    (2006.01)
*C06B 25/34*   (2006.01)
(Continued)

(52) U.S. Cl.
CPC .......... *B01D 9/0027* (2013.01); *A61K 31/194* (2013.01); *A61K 31/522* (2013.01);
(Continued)

(58) Field of Classification Search
CPC ...... B01D 9/0018; B01D 9/0027; B01D 1/16; B01D 1/18; B01D 9/0031
See application file for complete search history.

(56) References Cited

U.S. PATENT DOCUMENTS

| 3,361,523 A | 1/1968 | Shen Chung Yu |
| 4,482,641 A | 11/1984 | Wennerberg |

(Continued)

FOREIGN PATENT DOCUMENTS

| EP | 0 408 801 | 1/1991 |
| JP | S-59196746 | 11/1984 |

(Continued)

OTHER PUBLICATIONS

International Search Report for PCT/EP2015/065335, dated Sep. 23, 2015.
(Continued)

*Primary Examiner* — Theodore R. Howell
(74) *Attorney, Agent, or Firm* — B. Aaron Schulman, Esq.; Stites & Harbison, PLLC.

(57) ABSTRACT

The invention relates to a method for producing a cocrystal of at least two compounds by means of instantaneous evaporation or flash evaporation, for example for the production of cocrystals in the fields of energetic materials, pharmaceutical compounds, phytopharmaceutical com-
(Continued)

pounds, ferroelectric materials, non-linear response materials or bioelectronic materials.

27 Claims, 1 Drawing Sheet

(51) Int. Cl.
    *C06B 21/00*     (2006.01)
    *B01D 1/16*     (2006.01)
    *A61K 31/194*     (2006.01)
    *A61K 31/522*     (2006.01)
    *B01D 1/18*     (2006.01)

(52) U.S. Cl.
    CPC ............... *B01D 1/16* (2013.01); *B01D 1/18* (2013.01); *B01D 9/0018* (2013.01); *B01D 9/0031* (2013.01); *C06B 21/0091* (2013.01); *C06B 25/34* (2013.01)

(56) References Cited

U.S. PATENT DOCUMENTS

| | | | |
|---|---|---|---|
| 4,518,488 A | 5/1985 | Wennerberg | |
| 4,567,031 A | 1/1986 | Riley | |
| 4,795,330 A | 1/1989 | Noakes et al. | |
| 5,324,751 A | 6/1994 | Duross | |
| 6,001,262 A * | 12/1999 | Kelada | B01J 47/022 |
| | | | 210/278 |
| 6,236,946 B1 | 5/2001 | Scanlan et al. | |
| 7,628,893 B1 * | 12/2009 | Bonser | B01D 1/18 |
| | | | 159/2.1 |
| 8,617,588 B2 | 12/2013 | Tillotson et al. | |
| 9,358,212 B2 | 6/2016 | Tillotson et al. | |
| 9,439,914 B2 | 9/2016 | Ahmad et al. | |
| 9,513,183 B2 | 12/2016 | Thompson et al. | |
| 9,637,840 B2 | 5/2017 | Ruecroft et al. | |
| 9,682,043 B2 | 7/2017 | Goldman | |
| 10,280,124 B2 | 5/2019 | Ahmad et al. | |
| 2005/0181041 A1 | 8/2005 | Goldman | |
| 2008/0075777 A1 * | 3/2008 | Kennedy | B01D 9/0027 |
| | | | 424/484 |
| 2010/0226964 A1 | 9/2010 | Tillotson et al. | |
| 2011/0146678 A1 | 6/2011 | Ruecroft et al. | |
| 2012/0264917 A1 | 10/2012 | Saunders et al. | |
| 2013/0165371 A1 * | 6/2013 | Dobry | B01J 2/04 |
| | | | 514/5.9 |
| 2014/0093574 A1 | 4/2014 | Tillotson et al. | |
| 2015/0000846 A1 | 1/2015 | Risse et al. | |
| 2015/0313920 A1 | 11/2015 | Ahmad et al. | |
| 2015/0377733 A1 | 12/2015 | Thompson et al. | |
| 2016/0263036 A1 | 9/2016 | Tillotson et al. | |
| 2016/0347680 A1 | 12/2016 | Ahmad et al. | |
| 2017/0275781 A1 | 9/2017 | Ruecroft et al. | |

FOREIGN PATENT DOCUMENTS

| | | | |
|---|---|---|---|
| JP | 61046238 | 3/1986 | |
| JP | 07332847 | 12/1995 | |
| WO | WO 2013117671 A1 * | 8/2013 | ............... B01D 1/18 |

OTHER PUBLICATIONS

Written Opinion of the International Searching Authority for PCT/EP2015/065335, dated Sep. 23, 2015.
Preliminary Report dated Mar. 27, 2015 in corresponding French Application No. FR 1456461.

* cited by examiner

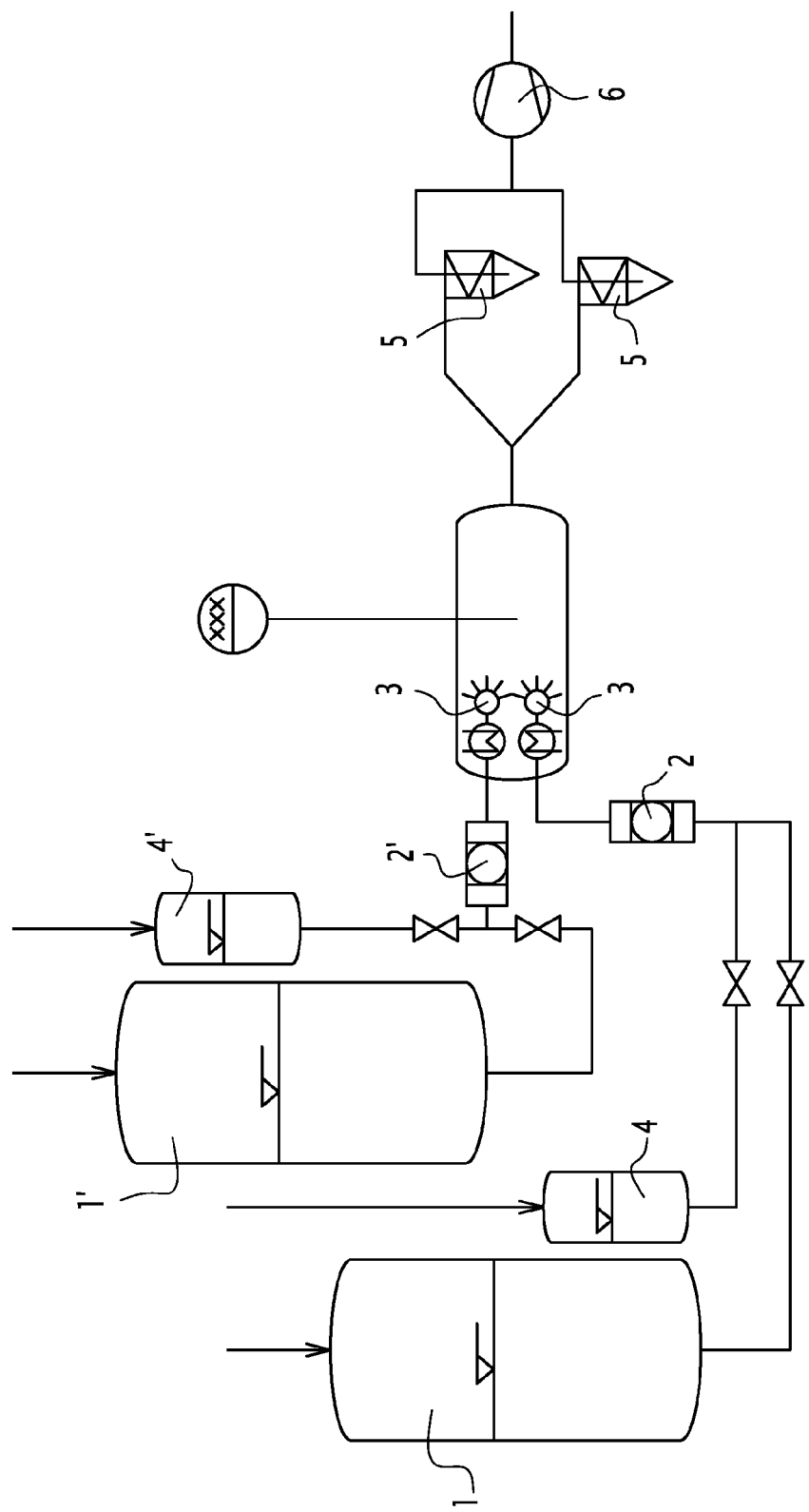

METHOD FOR PRODUCING COCRYSTALS BY MEANS OF FLASH EVAPORATION

The invention relates to a method for preparing a co-crystal of at least two compounds by instantaneous evaporation or flash evaporation, for example for preparing co-crystals in the fields of energy materials, pharmaceutical compounds, phytopharmaceutical compounds, ferroelectric materials, materials with a non-linear response or bio-electronic materials.

Co-crystals are solids assembled on a molecular scale. Several types of intermolecular interactions may allow the preparation of co-crystals. These interactions may be hydrogen bonds, ionic bonds, bonds of the stacking type ($\pi$ stacking) or further Van der Waals bonds.

Co-crystals are generally more stable thermodynamically than the initial compounds.

Co-crystals generally have improved properties as compared with the corresponding compounds used individually.

Thus, co-crystals of pharmaceutical or phytopharmaceutical substances, of energy materials or of ferroelectric materials have improved properties.

For example, co-crystals of pharmaceutical or phytopharmaceutical substances generally have better solubility and therefore better bioavailability. They also have improved stability, notably under humid conditions.

Also, co-crystals of energy materials have improved properties, notably better reactivity combined with reduced sensitivity, an essential property during their handling.

However, the methods for preparing co-crystals of the state of the art have drawbacks strongly limiting the development of the use of co-crystals.

Thus, the methods of the state of the art are not continuous or semi-continuous methods but methods for batch-wise preparation or batch methods. These methods of the state of the art therefore do not allow high yields.

Four types of methods of the state of the art give the possibility of preparing co-crystals.

Crystallization by slow evaporation of a concentrated solution of several compounds, the milling of reagents in the solid state optionally in the presence of a solvent, the electro-chemically induced reactions and the crystallization with controlled kinetics by rapid evaporation of the solvent of a solution of the pure compounds are known.

However, these methods do not allow the continuous or semi-continuous preparation of co-crystals.

Further, the co-crystals prepared according to the known methods are not always of sufficient quality.

The average size of the co-crystals prepared according to known methods is not always regular and is not systematically micrometric, submicrometric or nanometric. Further, the known methods do not give the possibility of attaining high crystallization rates.

Moreover, the RESS (Rapid Expansion of Supercritical Solutions) technology for the preparation of nanoparticles in a supercritical fluid is known. This technology is only efficient at a reduced scale and therefore cannot be transferred to the industrial level. Further, the preparation in a supercritical fluid does not give the possibility of controlling the stoichiometry. A method for preparing nanoparticles of a composite material is also known from the application WO 2013-117671. However, this method does not allow preparation of co-crystals.

Therefore there exists a need for having a method for preparing co-crystals providing a solution to the problems of the methods for preparing co-crystals of the state of the art.

Thus, the invention provides a method for preparing a co-crystal of at least two compounds by instantaneous evaporation or flash evaporation which gives the possibility of providing a solution to all or part of the problems of the methods of the state of the art.

The invention provides a method for preparing a co-crystal of at least two compounds bound through hydrogen bonds, ionic bonds, bonds of the stacking type ($\pi$-$\pi$ stacking) or Van der Waals bonds, comprising the successive steps:

preparation
  of a solution comprising at least one solvent and at least two organic, mineral or organometal compounds, which may be bound through hydrogen bonds, by ionic bonds, by bonds of the stacking type ($\pi$-$\pi$ stacking) or by Van der Waals bonds; or
  of at least two solutions each comprising at least one solvent and at least one organic, mineral or organometal compound, which may be bound through hydrogen bonds, by ionic bonds, by bonds of the stacking type ($\pi$-$\pi$ stacking) or by Van der Walls bonds;
heating of the solution or of the solutions, under a pressure ranging from 3 to 300 bars, at a temperature above the boiling point of the solvent or at a temperature above the boiling point of the mixture of solvents;
atomization of the solution or of the solutions in an atomization chamber by means of at least one dispersion device and under an angle ranging from 30 to 150° at a pressure ranging from 0.0001 to 2 bars;
separation of the solvent or of the solvents in gaseous form.

Preferably, the invention relates to a method comprising the successive steps:

preparing a solution comprising at least one solvent and at least two organic, mineral or organometal compounds, which may be bound through hydrogen bonds, ionic bonds, bonds of the stacking type ($\pi$-$\pi$ stacking) or through Van der Weals bonds;
heating the solution, under a pressure ranging from 3 to 300 bars, at a temperature greater than the boiling point of the solvent or at a temperature greater than the boiling point of the mixture of solvents;
atomization of the solution in an atomization chamber by means of at least one dispersion device and under an angle ranging from 30 to 150° at a pressure ranging from 0.0001 to 2 bars;
separation of the solvent in a gaseous form.

Also preferably, the invention relates to a method comprising the successive steps:

preparing at least two solutions each comprising at least one solvent and at least one organic, mineral or organometal compound, which may be bound through hydrogen bonds, ionic bonds, through bonds of the stacking type ($\pi$-$\pi$ stacking) or through Van der Weals bonds;
heating the solutions, under a pressure ranging from 3 to 300 bars, at a temperature above the boiling point of the solvent or at a temperature above the boiling point of the mixture of solvents;
atomization of the solutions in a same atomization chamber by means of at least one dispersion device and under an angle ranging from 30 to 150° at a pressure ranging from 0.0001 to 2 bars;
separation of the solvents in a gaseous form.

The method according to the invention is advantageously applied in a continuous or a semi-continuous way. Preferably, it is applied continuously.

Advantageously, the method according to the invention comprises the preparation of one or at least one solution comprising
- two to ten compounds; or
- two compounds; or
- two compounds in a molar ratio selected from among ¼, ⅓, ½, 1/1, 2/1, 3/1, 4/1; or
- three compounds; or
- three compounds in a molar ratio X/Y/Z wherein X, Y and Z, either identical or different, represent 1, 2, 3 or 4;
- four compounds; or
- four compounds in a molar ratio W/X/Y/Z wherein W, X, Y and Z, either identical or different, represent 1, 2, 3 or 4;
- five compounds; or
- five compounds in a molar ratio V/W/X/Y/Z wherein V, W, X, Y and Z, either identical or different, represent 1, 2, 3 or 4.

Preferably, the method according to the invention comprises the preparation of one or at least one solution comprising two, three or four compounds.

Also preferably, the method according to the invention comprises the preparation of at least two solutions each comprising at least one solvent and at least one organic, mineral or organometal compound, these compounds either identical or different, may be bound through hydrogen bonds, ionic bonds, bonds of the stacking type ($\pi$-$\pi$ stacking) or through Van der Waals bonds. These solutions may each independently comprise several of these compounds.

The method according to the invention is particularly advantageous for the preparation of co-crystals of compounds selected from among energy compounds, pharmaceutical compounds, phytopharmaceutical compounds, coloring compounds, pigments, inks, paints, metal oxides.

Preferably, the method according to the invention is applied for the preparation of co-crystals of compounds selected from among energy compounds, pharmaceutical compounds, phytopharmaceutical compounds.

Also advantageously, the method according to the invention gives the possibility of preparing co-crystals, the size of which is micrometric or which have at least one dimension of less than 500 µm, preferably which have at least one dimension of less than 100 µm.

Also advantageously, the method according to the invention gives the possibility of preparing co-crystals, the size of which is submicrometric or which have at least one dimension comprised between 100 and 1,000 nm.

Preferably, the method according to the invention gives the possibility of preparing co-crystals, the size of which is nanometric and which have at least one dimension of less than 100 nm.

More preferably, the co-crystals prepared according to the invention have a size ranging from 2 to 100 nm; or ranging from 5 to 90 nm; or ranging from 10 to 80 nm; or ranging from 50 to 300 nm; or ranging from 50 to 200 nm; or ranging from 50 to 120 nm; or ranging from 10 to 100 nm; or ranging from 60 to 100 nm.

Advantageously, the method according to the invention comprises the preparation of one or at least one solution comprising at least two organics, mineral or organometal compounds and at least two solvents.

Also advantageously, the method according to the invention comprises the preparation of one or at least one solution comprising at least one solvent of one of the compounds and at least one co-solvent of one of the compounds.

Also advantageously, the method according to the invention comprises the preparation of one or at least one solution comprising at least one solvent of one of the compounds and at least one anti-solvent of one of the compounds.

Preferably, the solvent(s) applied have a boiling point of less than 80° C. or less than 60° C. As a solvent, mention may be made of alkanes, for example pentane (PE=36° C.) or hexane (PE=68° C.); alcohols, for example methanol (PE=65° C.) or ethanol (PE=78-79° C.); thiols, for example ethane-thiol (PE=35° C.); aldehydes, for example ethanol (PE=20° C.) or propionic aldehyde (PE=48° C.); ketones, for example acetone (PE=56° C.); ethers, for example methyl-tert-butyl ether (PE=55° C.) or tetrahydrofurane (PE=66° C.); acid esters, notably the esters of formic acid, for example methyl formate (PE=32° C.), esters of acetic acid, for example methyl acetate (PE=57-58° C.); amines, for example trimethylamine (PE=2-3° C.).

Preferably, the method according to the invention comprises a final step for recovering the co-crystals of compounds.

More preferably, the recovery of the co-crystals of compounds is achieved by means of one or several devices selected from among an electrostatic separator, a cyclone, a cyclone comprising an electrostatic device.

The conditions for applying the method according to the invention may vary quite widely, notably depending on the compounds to be co-crystallized or else depending on the solvents used.

Advantageously, the heating of the solution is carried out under a pressure ranging from 5 to 150 bars or ranging from 10 to 60 bars. During the application of several solutions, the respective heating of each solution may be carried out under a pressure ranging from 5 to 150 bars or ranging from 10 to 60 bars which may be identical or different for each solution.

Also advantageously, the heating of the solution is carried out under the pressure of an inert gas selected from among nitrogen, argon, helium, neon, xenon.

During the atomization of the solution, the pressure is advantageously comprised between 0.001 and 2 bars.

The dispersion device applied during the atomization of the solution is advantageously selected from among a hollow cone nozzle, a solid cone nozzle, a flat jet nozzle, a rectilinear jet nozzle, a pneumatic atomizer and associations thereof. A hollow cone nozzle is particularly advantageous.

Generally, the atomization may be carried out under an angle which may vary quite widely.

The atomization angle may thus be close to 180°, for example 170° or further 150° or 120°.

Mention may also be made of a range of atomization angles ranging from 60 to 80°.

These conditions also apply during the atomization of at least two solutions.

The invention also relates to a device allowing the application of the method when it applies at least two solutions. Thus, the invention provides a device for crystallization of nanoparticles of at least two compounds which may be bound through hydrogen bonds, ionic bonds, through bonds of the stacking type ($\pi$-$\pi$ stacking) or through Van der Waals bonds, comprising
- at least two reactors each comprising
  - a supply of a solution of each compound and of at least one solvent;
  - at least one pressurization device which may range from 3 to 300 bars;
  - at least one heating device;
- an atomization chamber comprising
  - at least one device for dispersing the solution under an angle ranging from 30 à 150° and at a pressure ranging from 0.0001 to 2 bars;

at least one device for separating a solvent;
one or several devices for recovering nanoparticles of compounds, selected from among an electrostatic separator, a cyclone, a cyclone comprising an electrostatic device.

BRIEF DESCRIPTION OF THE DRAWING FIGURE

FIG. 1 is a schematic view of an exemplary embodiment of a device for preparing co-crystals according to the claimed invention.

An embodiment of a device according to the invention is illustrated by FIG. 1. The device consists of four main portions: a set of two tanks (1 and 1') for storing under a strong pressure, fluids containing the substance(s) to be crystallized, an atomization chamber comprising two integrated heated nozzles (3), two axial cyclones (5) mounted in parallel and allowing a semi-continuous production, a vacuum pump (6).

In the tanks (1 and 1') of 5 L containing the solvent with the solute, an overpressure of compressed nitrogen is applied. In a first phase, this overpressure gives the possibility of displacing the oxygen and prevents evaporation of the solvent. The volume flow rate in this system is induced by the overpressure of compressed nitrogen.

Filters (2 and 2') of 15 μm repel all the soluble impurities into the initial solution.

Two hollow cone nozzles (3), each equipped with an electric heating system, are installed side by side in the atomization chamber. The pressure, temperature and particle grain size parameters are controlled. The type of connection allows a fast change of the nozzles. The temperature of the electric heating is selected by the user and automatically regulated. The nozzles are oriented relatively to each other so that their jets interpenetrate each other.

A tank or pan of solvent (4) is filled with the same solvent as the tank (1) and is used for rinsing the conduit and the nozzle after use. Also, the tank or pan of solvent (4') is filled with the same solvent as the tank (1').

The axial cyclones (5) are installed in parallel. During the operation, only one cyclone is operating; the second cyclone is in a standby situation. By means of the centrifugal force, the solid particles are deposited inside the cyclone, the gas components leave the cyclone through a dip-tube. In order to empty the cyclone, the circuit leading towards the second cyclone is opened first, in order to then close the first circuit leading to the first cyclone.

The vacuum pump (6) ensures a permanent flow in the installation and allows extraction of the solvent vapors of the system.

The different aspects of the invention are illustrated by the following examples.

EXAMPLE 1: PREPARATION OF CO-CRYSTALS FROM A SOLUTION

Co-crystals according to the invention were prepared from caffeine and oxalic acid or glutaric acid. Other co-crystals according to the invention were prepared from 2,4,6,8,10,12-hexanitro-2,4,6,8,10,12-hexaazaiso-wurtzitane (CL-20) and from 2,4,6-trinitrotoluene (TNT) or 1,3,5,7-tetranitro-1,3,5,7-tetrazacyclooctane (HMX).

Comparative examples were prepared from 2,4,6-trinitrotoluene (TNT) and from 1,3,5,7-tetranitro-1,3,5,7-tetrazacyclooctane (HMX).

Co-crystals were prepared in a continuous way by means of the device described in the international patent application WO-2013/117671 according to a method for instantaneous evaporation of a solution of the compounds to be co-crystallized which is overheated and compressed. During the method, the solution undergoes a very strong drop in pressure upon being atomized by means of a hollow cone nozzle.

The compounds to be co-crystallized are dissolved in a solvent for which the boiling point is generally less than 60° C. The compounds and the solvents as well as the reaction parameters applied are shown in table 1.

The solution is compressed (40 to 60 bars) and then atomized in an atomization chamber by means of a heated hollow cone nozzle.

The pressure in the atomization chamber (5 mbars) is obtained by means of a vacuum pump (35 m$^3$/h).

The sudden pressure drop causes displacement of the thermodynamic equilibrium making the overheated solution unstable. The solvent is instantaneously evaporated and co-crystals form.

The strong drop in pressure is accompanied by a strong drop of the temperature which is lowered to about 200° C. giving the possibility of protecting the co-crystals formed.

The continuous separation of the co-crystals formed is achieved by means of axial cyclones mounted in parallel.

TABLE 1

| | Examples | | | | | |
| --- | --- | --- | --- | --- | --- | --- |
| | according to the invention | | | | comparative | |
| | 1 | 2 | 3 | 4 | 1 | 2 |
| Compounds | caffeine/oxalic acid | caffeine/glutaric acid | TNT/CL20 | HMX/CL20 | TNT/HMX | TNT/HMX |
| Molar ratio | 2/1 | 1/1 | 1/1 | 1/2 | 1/1 | 1/2 |
| Solvent | acetone | acetone | acetone | acetone | acetone | acetone |
| Amount (g) | 3.5/0.8 | 4.8/3.2 | 2.4/1.2 | 2.7/8.0 | 3.4/4.5 | 2.2/5.7 |
| Concentration of the solution (% by mass) | 1.0 | 2.0 | 1.0 | 2.7 | 2.0 | 2.0 |
| Volume of the solution (mL) | 500 | 500 | 460 | 500 | 500 | 500 |
| Temperature of the nozzle (° C.) | 160 | 160 | 170 | 170 | 160 | 160 |
| Temperature of the cyclones (° C.) | 80 | 80 | 50 | 80 | 80 | 80 |

TABLE 1-continued

| | Examples | | | | | |
|---|---|---|---|---|---|---|
| | according to the invention | | | | comparative | |
| | 1 | 2 | 3 | 4 | 1 | 2 |
| Diameter of the cyclones (μm) | 60 | 60 | 60 | 60 | 60 | 60 |
| Pressure (bars) | 40 | 40 | 40 | 50 | 50 | 40 |
| Duration (mins) | 68 | 56 | 60 | 44 | 41 | 62 |
| Amount of co-crystals (g) | 2.77 | 5.13 | 1.59 | 4.93 | 0 | 0 |
| Amount of composites (g) | <LD | <LD | <LD | <LD | 5.35 | 4.85 |
| Yield (%) | 64.7 | 64.1 | 43.8 | 46.1 | 67.8 | 60.6 |

<LD: less than the detection limit in XRD

The products were characterized by AFM microscopy (Atomic Force Microscopy) at room temperature and at atmospheric pressure in order not to alter the co-crystals formed.

The average grain size distribution of the particles was evaluated. The average size of the caffeine/glutaric acid co-crystals (1/1) is 111 nm. The average size of the HMX/CL20 co-crystals (½) is 59 nm.

X-ray diffraction spectra were achieved for characterizing the co-crystals.

The obtained spectra were compared with spectra of the used initial products. The spectra of the co-crystals are different from the spectra of the initial products for the co-crystals formed. They correspond to the spectra of the Cambridge structural data bank or to the spectra available in the literature.

For the TNT/HMX composites (1/1 and ½), the X-ray diffraction spectra always have the characteristic lines of TNT alone as well as certain lines of HMX. The absence of certain lines of HMX indicates that HMX is present in an amorphous form. The TNT/HMX composites (1/1 and ½) are therefore mixtures of TNT crystals and of amorphous HMX.

The heat properties of the co-crystals were studied by Differential Scanning calorimetry (DSC).

The heating (5° C./min) of the TNT/CL20 co-crystals (1/1) shows the absence of the characteristic melting signal of pure TNT at 80° C., the TNT being within the lattice of the co-crystal with CL20. The characteristic melting temperature measured for the TNT/CL20 co-crystal (1/1) is of 135° C.

After the first phase of the DSC analysis, the temperature is reduced and then again increased. During the second heating, the thermal signal of TNT is again present at 80° C. confirming the dissociation of the co-crystal under the action of heat during the first heating followed by crystallization of pure TNT.

The heating of the caffeine/oxalic acid co-crystals (2/1) shows the presence of a thermal signal at 199° C. which is intermediate between the boiling points of both compounds pure caffeine and oxalic acid.

Continuation of the heating leads to the dissociation of the co-crystal. Next, the cooling followed by the second heating shows the presence of the thermal signal of pure caffeine.

For the TNT/HMX composites (1/1 and ½) of the comparative examples, the thermal signal of TNT is present as soon as the first heating. Next, this signal is not modified during the second heating. The TNT/HMX composites (1/1 and ½) are therefore simple physical mixtures of TNT and HMX particles. The TNT and HMX molecules cannot form intermolecular bonds for giving a co-crystal.

EXAMPLE 2: PREPARING CO-CRYSTALS FROM TWO SOLUTIONS

Co-crystals according to the invention were prepared continuously from HMX and CL20 by means of the device of FIG. 1.

5 g of CL20 dried beforehand in 250 ml of acetone (CHROMASOLV® HPLC quality ≥99.9% from Sigma Aldrich) are dissolved. Moreover, 1.35 g of HMX dried beforehand in 250 ml of acetone (CHROMASOLV® HPLC quality ≥99.9% from Sigma Aldrich) are dissolved.

Each solution is stirred and then sonicated with ultrasonic waves for 10 seconds. Next, each solution is poured in a tank of 1 L: the acetone solution with CL20 in the tank 1 and the acetone solution with HMX in the tank 1'. To each tank 1 and 1' is connected in parallel a tank of technical acetone, indicated by the numbers 2 and 2'. All the tanks are closed and pressurized at 40 bars by injecting pressurized nitrogen. The pressure is measured before the the nozzle and controlled all along the reaction.

The vacuum is applied in the whole system by starting the pump. Once the vacuum is stabilized at about 0.1 mbar, one of the two cyclones is isolated from the system.

The valves connecting the tanks 2 and 2' are open and the heating systems are started and regulated for the nozzles to 170° C. and for the cyclones to 80° C. Once the temperatures are stabilized, the cyclone used is isolated and the other isolated cyclone is open. Then the solutions of the tanks 1 and 1' are sprayed.

After 20 minutes, the cyclones are again reversed and then the valves supplying the nozzles are switched onto the tanks 2 and 2' of technical acetone. The heating systems are then stopped.

During the cooling, the co-crystal CL20-HMX is recovered in the cyclone having been used when the solutions 1 and 1' were sprayed. Once the temperatures are below 50° C., the inflows of technical acetone are cut and the vacuum pump is stopped after having allowed the pressure to rise again. Some CL20-HMX 2:1 co-crystal is thereby formed in situ at 2.67% by weight in solution by instantaneous evaporation or flash evaporation with multi-nozzles.

The product was characterized by AFM microscopy (Atomic Force Microscopy) at room temperature and at atmospheric pressure in order not to alter the co-crystal formed.

The average grain size distribution of the particles was evaluated. The average size of the CL20-HMX (2/1) cocrystal is 60 nm. An X-ray diffraction spectrum was produced for characterizing the co-crystal. The obtained spectrum was compared with spectra of the initial products used and with that of the co-crystal obtained in Example 1. The spectrum has all the characteristic lines of the CL20-HMX (2/1) co-crystal whether it is compared with the literature or with the CL20-HMX (2/1) co-crystal obtained in Example 1. The spectrum also has the characteristic lines of the beta phase of CL20.

The invention claimed is:

1. A method for preparing a co-crystal of at least two compounds, comprising:
   providing at least two organic, mineral, or organometal compounds which may be bound each other by hydrogen bonds, ionic bonds, bonds of the stacking type (π-π stacking) or Van der Waals bonds;
   preparing a solution comprising at least one solvent and said at least two compounds to be co-crystalsized, wherein said preparation comprises dissolving said at least two compounds in said at least one solvent;
   heating the solution, under a pressure ranging from 3 to 300 bars, at a temperature above the boiling point of the solvent or at a temperature above the boiling point of the mixture of solvents;
   atomizing the solution in an atomization chamber with at least one dispersion device and under an angle ranging from 30 to 150° at a pressure ranging from 0.0001 to 2 bars;
   separating the solvent or solvents in gaseous form; and
   obtaining at least a co-crystal of said at least two compounds assembled on a molecular scale.

2. The method according to claim 1 wherein said at least two compounds are selected from the group consisting of:
   two to ten compounds;
   two compounds;
   two compounds in a molar ratio selected from the group consisting of ¼, ⅓, ½, 1/1, 2/1, 3/1, and 4/1;
   three compounds;
   three compounds in a molar ratio X/Y/Z wherein X, Y and Z, either identical or different, represent 1, 2, 3 or 4;
   four compounds;
   four compounds in a molar ratio W/X/Y/Z wherein W, X, Y and Z, either identical or different, represent 1, 2, 3 or 4;
   five compounds; and
   five compounds in a molar ratio V/W/X/Y/Z wherein V, W, X, Y and Z, either identical or different, represent 1, 2, 3 or 4.

3. The method according to claim 1 wherein said co-crystal:
   is of a micrometric size; or
   has at least one dimension of less than 500 μm; or
   has at least a dimension of less than 100 μm; or
   is of submicrometric size; or
   has at least one dimension comprised between 100 nm and 1,000 nm; or
   is of a nanometric size; or
   has at least one dimension of less than 100 nm; or
   is of a size ranging from 2 to 100 nm; or
   is of a size ranging from 5 to 90 nm; or
   is of a size ranging from 10 to 80 nm; or
   is of a size ranging from 50 to 300 nm; or
   is of a size ranging from 50 to 200 nm; or
   is of a size ranging from 50 to 120 nm; or
   is of a size ranging from 10 to 100 nm; or
   is of a size ranging from 60 to 100 nm.

4. The method according to claim 1, comprising the preparation of one solution comprising said at least two compounds and at least two solvents or at least one solvent and at least one co-solvent or at least one solvent and at least one anti-solvent of one of the compounds.

5. The method according to claim 1, further comprising recovering said co-crystals using one or more devices selected from the group consisting of an electrostatic separator, a cyclone, and a cyclone comprising an electrostatic device.

6. The method according to claim 1 wherein said method is continuous or semi-continuous.

7. The method according to claim 1, wherein the solvent or of the mixture of solvents has a boiling point of less than 80° C. or less than 60° C.

8. The method according to claim 1, wherein heating of the solution is carried out under a pressure ranging from 5 to 150 bars or ranging from 10 to 60 bars.

9. The method according to claim 1, wherein heating of the solution is carried out under the pressure of an inert gas selected from the group consisting of nitrogen, argon, helium, neon, and xenon.

10. The method according to claim 1, wherein atomization of the solution is carried out at a pressure ranging from 0.001 to 2 bars.

11. The method according to claim 1, wherein the dispersion device is selected from the group consisting of a hollow cone nozzle, a solid cone nozzle, a flat jet nozzle, a rectilinear jet nozzle, a pneumatic atomizer, and combinations thereof.

12. The method according to claim 1, wherein the dispersion device is a hollow cone nozzle.

13. The method according to claim 1, wherein the compound is selected from the group consisting of energy compounds, pharmaceutical compounds, phytopharmaceutical compounds, coloring compounds, pigments, inks, paints, and metal oxides.

14. The method according to claim 1, wherein the solvent is selected from the group consisting of alkanes; alcohols; thiols; aldehydes; ketones; ethers; acid esters; amines; and any mixture thereof.

15. A method for preparing a co-crystal of at least two compounds comprising successively:
   providing at least two organic, mineral, or organometal compounds which may be bound each other by hydrogen bonds, ionic bonds, bonds of the stacking type (π-π stacking) or Van der Waals bonds;
   preparing at least two solutions each comprising at least one solvent and said at least one compound, wherein each preparation comprises dissolving said compound in said solvent;
   heating the solutions, under a pressure ranging from 3 to 300 bars, at a temperature above the boiling point of the solvent or at a temperature above the boiling point of the mixture of solvents;
   atomizing the solutions in a same atomization chamber with at least one dispersion device and under an angle ranging from 30 to 150° at a pressure ranging from 0.0001 to 2 bars;
   separating the solvents in a gaseous form; and
   obtaining at least a co-crystal of said at least two compounds assembled on a molecular scale.

16. The method according to claim 15 wherein said at least two compounds are selected from the group consisting of:
   two to ten compounds;
   two compounds;

two compounds in a molar ratio selected from the group consisting of ¼, ⅓, ½, 1/1, 2/1, 3/1, and 4/1;

three compounds;

three compounds in a molar ratio X/Y/Z wherein X, Y and Z, either identical or different, represent 1, 2, 3 or 4;

four compounds;

four compounds in a molar ratio W/X/Y/Z wherein W, X, Y and Z, either identical or different, represent 1, 2, 3 or 4;

five compounds; and five compounds in a molar ratio V/W/X/Y/Z wherein V, W, X, Y and Z, either identical or different, represent 1, 2, 3 or 4.

17. A method according to claim 15 wherein said co-crystal:

is of a micrometric size; or has at least one dimension of less than 500 μm; or has at least a dimension of less than 100 μm; or is of submicrometric size; or has at least one dimension comprised between 100 nm and 1,000 nm; or is of a nanometric size; or has at least one dimension of less than 100 nm; or is of a size ranging from 2 to 100 nm; or is of a size ranging from 5 to 90 nm; or is of a size ranging from 10 to 80 nm; or is of a size ranging from 50 to 300 nm; or is of a size ranging from 50 to 200 nm; or is of a size ranging from 50 to 120 nm; or is of a size ranging from 10 to 100 nm; or is of a size ranging from 60 to 100 nm.

18. The method according to claim 15, further comprising recovering said co-crystals of compounds using one or several devices selected from the group consisting of an electrostatic separator, a cyclone, and a cyclone comprising an electrostatic device.

19. The method according to claim 15 wherein said method is continuous or semi-continuous.

20. The method according to claim 15, wherein the solvent or of the mixture of solvents has a boiling point of less than 80° C. or less than 60° C.

21. The method according to claim 15, wherein heating of the solutions is carried out under a pressure ranging from 5 to 150 bars or ranging from 10 to 60 bars.

22. The method according to claim 15, wherein heating of the solutions is carried out under the pressure of an inert gas selected from the group consisting of nitrogen, argon, helium, neon, and xenon.

23. The method according to claim 15, wherein atomization of the solutions is carried out at a pressure ranging from 0.001 to 2 bars.

24. The method according to claim 15, wherein the dispersion device is selected from the group consisting of a hollow cone nozzle, a solid cone nozzle, a flat jet nozzle, a rectilinear jet nozzle, a pneumatic atomizer, and combinations thereof.

25. The method according to claim 15, wherein the dispersion device is a hollow cone nozzle.

26. The method according to claim 15, wherein the compound is selected from the group consisting of energy compounds, pharmaceutical compounds, phytopharmaceutical compounds, coloring compounds, pigments, inks, paints, and metal oxides.

27. The method according to claim 15, wherein the solvent is selected from the group consisting of alkanes; alcohols; thiols; aldehydes; ketones; ethers; acid esters; amines; and any mixture thereof.

* * * * *